United States Patent [19]

Smith

[11] Patent Number: 5,033,674
[45] Date of Patent: Jul. 23, 1991

[54] FRAGRANCE DISPENSER

[75] Inventor: Douglas B. Smith, New Canaan, Conn.

[73] Assignee: Avon Products, Inc., New York, N.Y.

[21] Appl. No.: 527,539

[22] Filed: May 23, 1990

[51] Int. Cl.⁵ ............................................. A61L 9/04
[52] U.S. Cl. ...................................... 239/58; 239/34
[58] Field of Search ........................ 239/51.5, 52–60, 239/34

[56] References Cited

U.S. PATENT DOCUMENTS

| | | | |
|---|---|---|---|
| 439,317 | 10/1890 | Allen | 239/55 |
| 2,247,600 | 7/1941 | Brennan et al. | 239/57 |
| 2,738,225 | 3/1956 | Meek | 239/59 |
| 4,219,145 | 8/1980 | Jaeschke et al. | 239/59 |
| 4,258,874 | 3/1981 | Webinger et al. | 239/59 |

FOREIGN PATENT DOCUMENTS 835668  5/1960  United Kingdom ............... 239/58

Primary Examiner—Andres Kashnikow
Assistant Examiner—Karen B. Merritt
Attorney, Agent, or Firm—Hopgood, Calimafde

[57] ABSTRACT

A fragrance dispenser is provided comprising a container for storing a fragrance releasing substance. The container has a first and second end, and a side wall surface with one or more apertures formed therein. The fragrance dispenser also includes a flexible covering disposed over the side wall surface, having a plurality of slits formed therein. In general, the flexible covering is fixedly attached to a portion of a side wall surface and has a free portion which is slidable relative to the side wall surface. In the open configuration, the flexible covering distorts into a structure which envelops a substantial portion of the container and provides a plurality of passages through which fragrance vapor flows to the ambient environment.

11 Claims, 3 Drawing Sheets

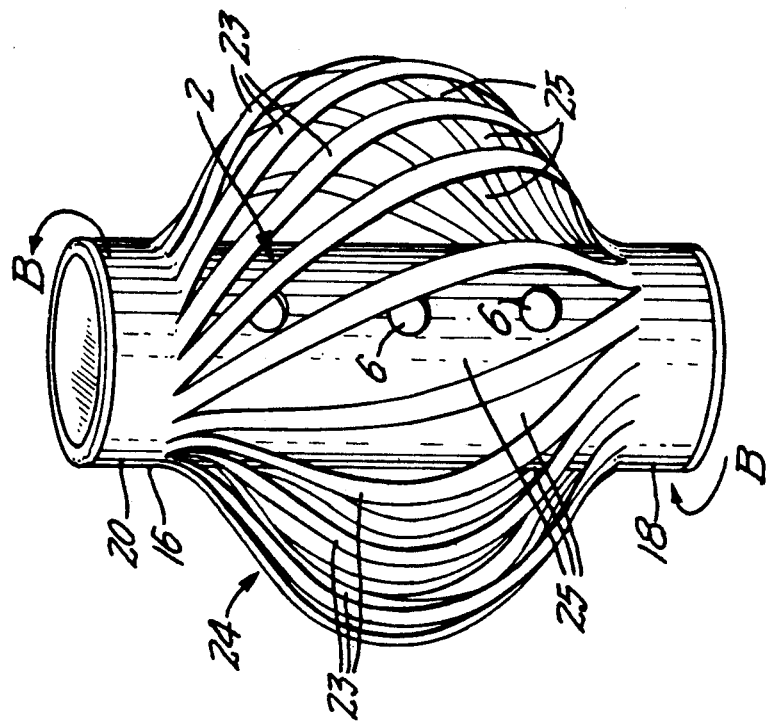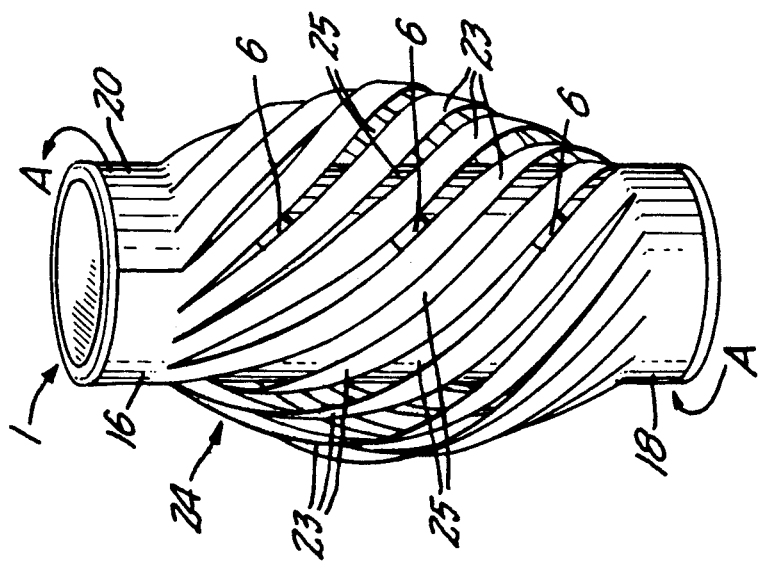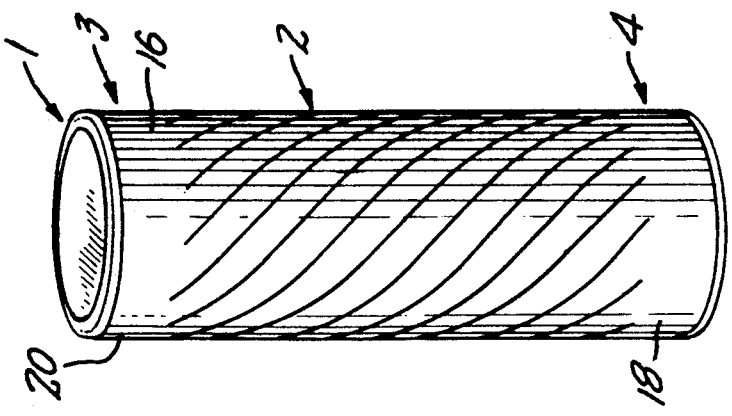

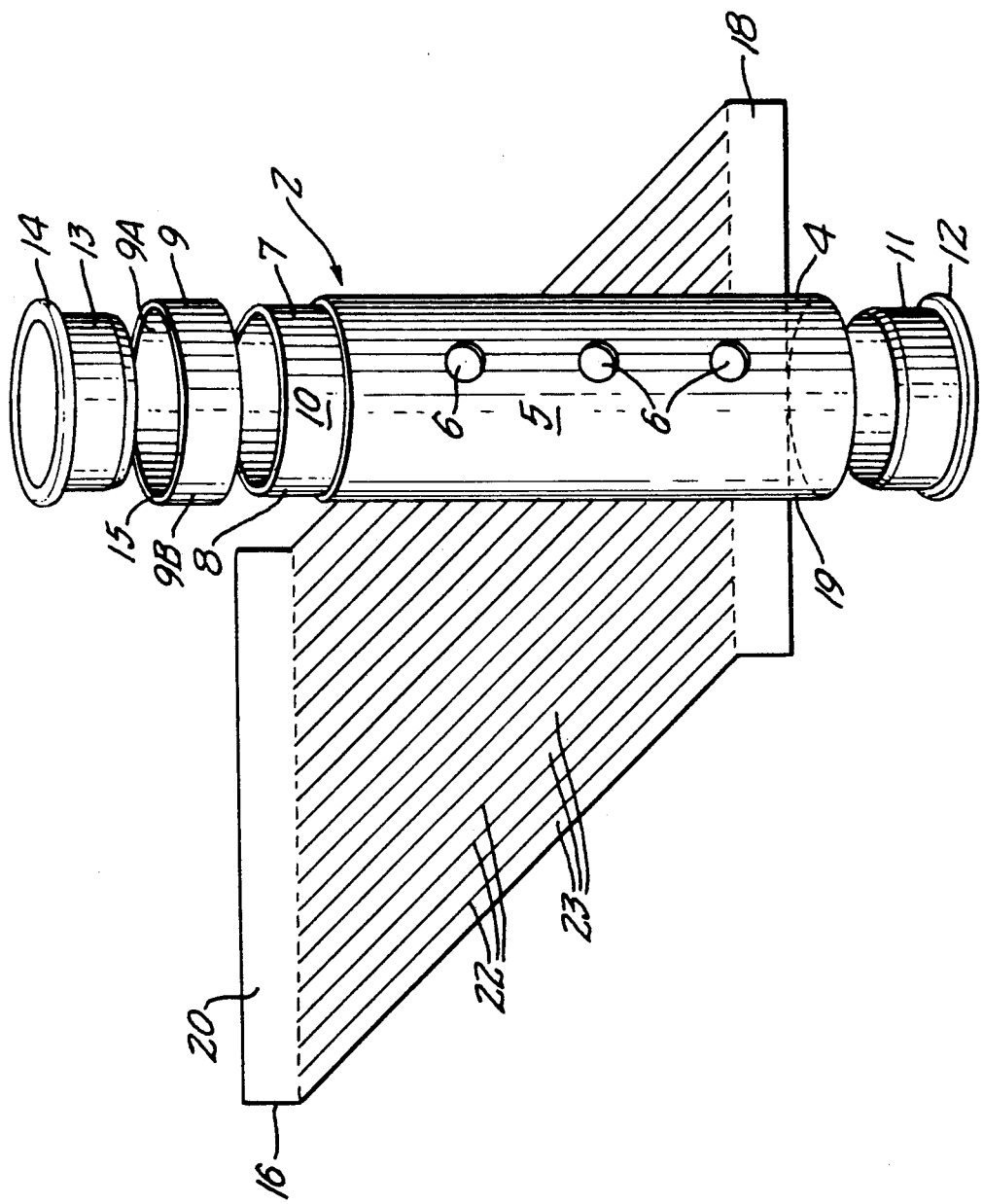

FRAGRANCE DISPENSER

BACKGROUND OF THE INVENTION

1. Field of Invention

The present invention generally relates to devices for dispensing a fragrance by employing principles of either evaporation or sublimation and, more particularly, devices which provide adjustable control over the release of the fragrance to the ambient environment, while providing a decorative effect having aesthetic and artistic appeal.

2. The Brief Description of Prior Art

A wide variety of devices are presently known for dispensing both liquid and solid fragrances to the environment of rooms, automobiles and the like. One type of dispenser which has enjoyed popularity over the years is constructed by placing a fragrance release agent in a carrying container having a plurality of apertures (e.g., holes) in its side wall surfaces. The carrying container is positioned inside an outer sleeve having a plurality of apertures in its side wall surfaces. The inner fragrance carrying container is typically adapted for slidable rotation or translational movement relative to the outer sleeve for establishing coincidence or registration of the apertures in the fragrance carrying container and outer sleeve. In this registered position the corresponding apertures allow the fragrance vapor to escape from the dispenser to the outside environment. Examples of these prior art devices can be found in U.S. Pat. Nos. 439,317; 2,038,071; 2,247,600; 2,738,225; 4,219,145; 4,258,874 and Des. 262,821. Each suffer from several significant shortcomings and drawbacks.

In particular, the prior art fragrance dispensers substantially maintain their overall geometrical shape and appearance in the dispensing and non-dispensing configurations. This condition provides a limited degree of control over the release of vapors to the environment. In other words, the prior art did not provide a fragrance dispenser which is capable of undergoing a substantial change in physical appearance or overall geometry, to provide a decorative structure which facilitates opening and closing of the dispenser to permit a desired degree of passive fragrancing to the ambient environment.

Accordingly, it is the primary object of the present invention to provide a fragrance dispenser having a physical appearance and overall geometry which undergoes substantial transformation when closed and opened, to permit a desired degree of passive fragrancing of an environment.

It is another object of the present invention to provide a fragrance dispenser having a cylindrical geometry in its closed position and, in its open dispensing position, a decorative enveloping structure of oblate spherical geometry, which is generated abut a substantial portion of a cylindrical inner fragrance carrying container.

Another object of the present invention is to provide a fragrance dispenser in which the decorative enveloping structure of oblate spherical geometry comprises a plurality of helically extending strips generated about the cylindrical inner fragrance carrying container.

Other and further objects of the present invention will be explained and will become apparent to one with ordinary skill in the art to which the present invention pertains.

SUMMARY OF THE INVENTION

In accordance with the principles of the present invention, a fragrance dispenser is provided generally comprising a container for storing a fragrance releasing substance which produces fragrance vapor. The container has a first and second end and a side wall surface with one or more apertures formed therein. The fragrance dispenser also includes a flexible covering disposed over the side wall surface and having a plurality of slits formed therein. In general, the flexible covering is fixedly attached to a portion of the side wall surface and has a free portion which is slidable relative to the side wall surface to form a structure which envelops a substantial portion of the container and provides a plurality of passages through which fragrance vapor can flow. By distorting the flexible covering into the enveloping structure, fragrance vapor within the container is permitted to flow freely through the apertures in the container and through the passages of the enveloping structure to the ambient atmosphere.

In the preferred embodiment the enveloping structure created by distortion of the flexible covering comprises a plurality of a flexible strips spaced substantially uniformly about the container. The plurality of passages are formed between adjacent flexible strips, through which fragrance vapor is permitted to flow. Each flexible strip of the enveloping structure has a lower end portion and an upper end portion. The lower end portion is preferably connected to a portion of the flexible covering which is fixedly attached to the side wall surface, whereas the upper end portion is preferably connected to a portion of the flexible covering which is free to slide relative to the side wall surface.

In one embodiment of the present invention, the container has a cylindrical geometry, and the plurality of slits in the flexible covering extend helically about the cylindrical container and divide the flexible covering into a plurality of helical strips. In such an embodiment, when the upper portion of the flexible covering is rotated counter-clockwise relative to side wall surface of the cylindrical container, the helically extending strips are distorted and transformed into an enveloping structure generally having an oblate spherical geometry. In this configuration, the helically extending strips provide a plurality of passages through which fragrance vapor can freely flow to the ambient environment. These passages in the enveloping structure have dimensions which can be varied in response to the rotation of the flexible covering relative to the side wall surface of the cylindrical container.

As a result of the present invention, it is now possible to achieve the closing (i.e., non-dispensing) and opening (i.e., dispensing) functions of a fragrance dispenser, while substantially altering, for purposes of aesthetic and artistic appeal, the overall geometry and general appearance of the fragrance dispenser.

BRIEF DESCRIPTION OF THE DRAWINGS

Reference is now made to the following detailed description of the preferred embodiments in connection with the accompanying drawings.

FIG. 1A is a perspective view of a first embodiment of the fragrance dispenser of the present invention, shown in its closed, non-dispensing configuration;

FIG. 1B is a perspective view of the fragrance dispenser in its partially-open, dispensing configuration;

FIG. 1C is a perspective view of the fragrance dispenser shown in its fully-open, dispensing configuration;

FIG. 2 is an exploded view of the fragrance dispenser showing the components of this particular embodiment;

DETAILED DESCRIPTION OF THE PREFERRED EMBODIMENT

Figure 4:
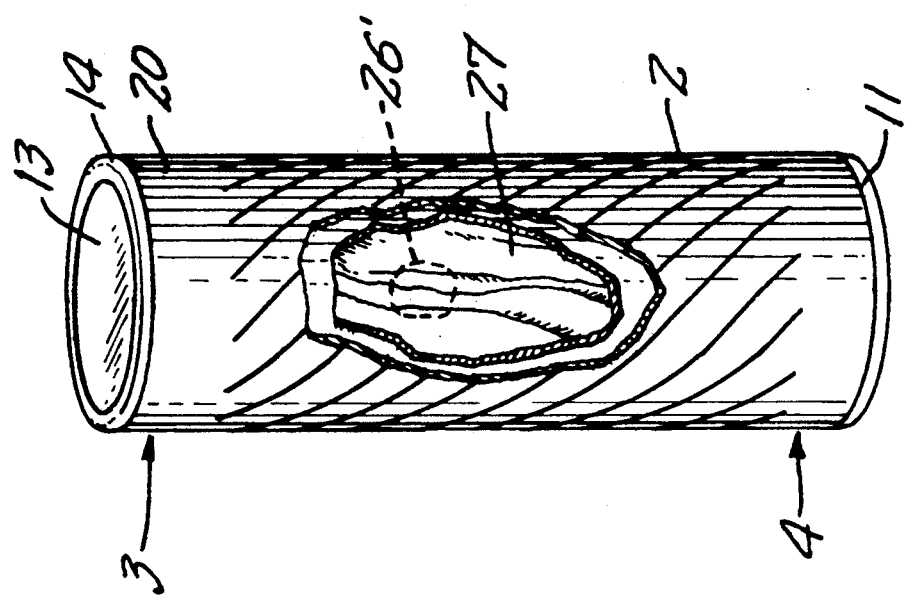
FIG. 4 is a perspective view of the fragrance dispenser, partially cut-away to show the fragrance dispensing material of the illustrative embodiment.

Referring to FIGS. 1A, 1B, 1C, 2, 3 and 4, one embodiment of the fragrance dispenser is generally indicated by 1 and will now be described as follows.

The fragrance dispenser 1 comprises a fragrance carrying container 2, which preferably is of a cylindrical geometry as shown. The fragrance carrying container 2 has a top (i.e., first) and bottom (i.e. second) portion indicated by reference numerals 3 and 4, respectively. The fragrance carrying container 2 also has a cylindrical side wall surface generally designated by reference numeral 5. In the side wall surface 5, a plurality of apertures 6 are provided which communicate with the interior volume of the container. A fragrance releasing material is placed in the container during manufacture. In the illustrated embodiment shown in FIG. 4, the fragrance releasing material comprises a high-absorbency polyethylene tablet 26 impregnated with a fragrance oil having a desired scent. The carrier tablet 26 is available from the Interflow Division of Chromex, Inc., Brooklyn, New York, as Product No. D-50. Fragrance oils are commercially available from a wide variety of vendors. As shown, the fragrance releasing tablet 26 is wrapped in a polyester fiber batting 27 which is folded over and inserted within the fragrance carrying container 2. When exposed to air, the tablet 26 releases fragrance vapor.

Figure 3:
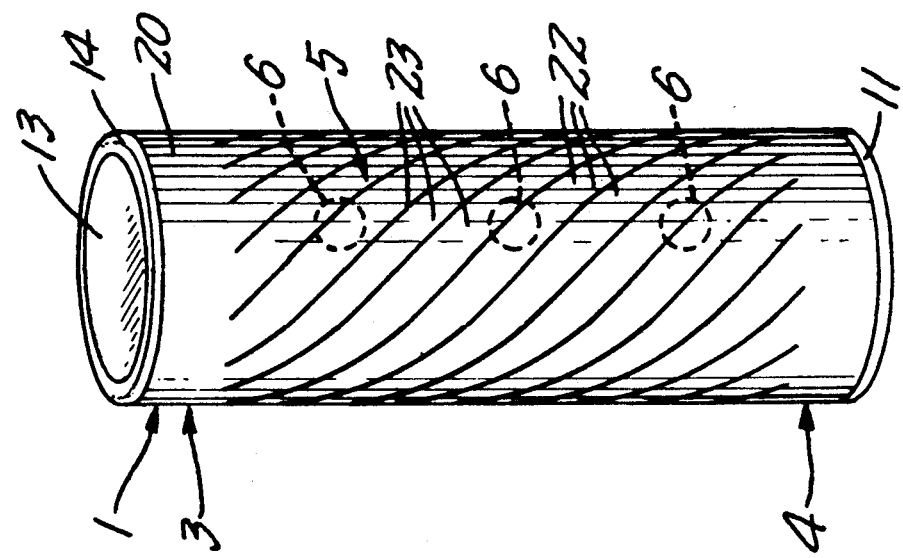
FIG. 3 is a perspective view of the fragrance dispenser constructed from the components illustrated in FIG. 2.

Along the peripheral surface 7 of the top portion of side wall surface 5, an annular shaped recess (i.e., groove) 8 is formed so that an annular ring 9 can be slid over the peripheral surface 7 of the top portion and within the annular recess 8 for rotational movement thereabout. Preferably, the inner bearing surface 9A of the annular ring 9 and the outer bearing surface 10 of the annular recess 8 each have a surface texture which provides desired frictional engagement between the annular recess 8 and the annular ring 9. This friction ensures that the annular ring 9 is maintained in its required position within the annular recess 8, during dispensing and non-dispensing operations. In order to close off the bottom end 4 of the fragrance carrying container 2, an end cap 11 with an annular flange 12 is installed into the bottom end 4, as illustrated in FIGS. 2 and 3. Similarly, in order that the rotatable annular ring 9 is maintained within the annular recess 8, and the fragrance releasing substance 26 is contained within the container 2, a top end cap 13 having an annular flange 14 is installed into the top end portion 3 of the container, as illustrated in FIGS. 2 and 3. The annular flange 14 of top end cap 13 extends sufficiently over end edge surface 15 of annular ring 9 to maintain the ring within the annular recess 8.

As illustrated in FIGS. 2 and 3, a flexible outer covering 16 made from plastic, paper or other suitable material is disposed over side wall surface 5 of cylindrical container 2 and outer surface 9B of annular ring 9, so as to lie snugly there against in the closed, non-dispensing configuration. The bottom portion of the outer flexible covering, generally indicated by reference numeral 18 and delineated by the dotted lines shown, is secured to the adjacent bottom portion 19 of side wall surface 5 using a layer of conventional adhesive. The top portion of the flexible outer covering 16, generally indicated by reference numeral 20 and delineated by the dotted lines shown, is secured to the adjacent outer surface 9B of annular ring 9, again using a layer of conventional adhesive.

As illustrated in FIGS. 2 and 3, a plurality of slits 22 are formed in flexible covering 16 over the portion defined between the dotted lines shown in FIG. 2. These slits 22 divide the flexible covering 16 into a plurality of helical strips 23 which extend about the cylindrical container 2. When the fragrance dispenser 1 is assembled and disposed in its closed, non-dispensing configuration shown in FIGS. 1A and 3, the helical strips 23 of flexible covering 5 cover the apertures 6 formed in the side wall surface of the container and prevent release of the fragrance.

To illustrate the fragrance dispensing function of the present invention, reference is made to FIGS. 1B and 1C. As shown in FIG. 1B, when annular ring 8 is rotated about 45° relative to side wall surface 5 (i.e., to position A), the helically extending strips 23 are thrust outwardly away from side wall surface 5 and apertures 6, and are otherwise distorted or transformed into a structure "enveloping" cylindrical fragrance carrying container 2. As shown in this partially opened configuration, the resulting enveloping structure generally indicated by reference numeral 24 approximates an oblate ellipsoid which is generated about, and appears to intersect with, a substantial portion of the cylindrical fragrance carrying container 2. This decorative enveloping structure 24 comprises an arrangement of distorted helical strips 23 which are spaced substantially uniformly about cylindrical container 2 and form passages 25 between adjacent helical strips. In this partially opened configuration illustrated in FIG. 1B, the fragrance vapor within container 2 is permitted to flow freely and passively through apertures 6 and passages 25 of enveloping structure 24 to the surrounding environment.

As illustrated in FIG. 1C, the fragrance dispenser 1 is fully-opened by rotating annular ring 8 and upper end portion 20 of the flexible covering about 90° relative to side wall surface 5 (i.e., from position A to B). Due to the distortion inherently imposed on helical strips 23, the dimensions of passages 25 of enveloping structure 24 can be selectively varied by rotating flexible covering 16 relative to side wall surface 5. When fully opened, the resulting geometry of the decorative enveloping structure 24 is approximate to that of an oblate spheroid which is generated about, and appears to intersect with, a substantial portion of the cylindrical fragrance carrying container 2.

The fragrance dispensers of the present invention may be made from a wide variety of materials, including cellulose, paper board and/or plastic materials, structured in accordance with the principles of the present invention and in a manner known to those skilled in the art. In the preferred embodiment, the flexible outer covering 16 can be made from a metallized polyester film bearing a geometric pattern. When the fragrance dispenser is opened, the geometric pattern as well as the flexible outer covering is transformed to provide a three dimensional decorative structure having aesthetic and artistic appeal.

In view of the present disclosure, a variety of modifications to the present invention are possible. For example, along the peripheral surface of the top portion of the cylindrical container, an annular shaped recess of extended length can be formed permitting an annular ring to be slid thereover. Notably, the annular recess can be provided with a longitudinally extending rib or flange which is adapted to be received within a longitudinal extending groove formed on the inside bearing surface of the annular ring. The purpose of the flange is to guide the annular ring when it is selectively moved up and down within the recess during the opening and closing functions attendant to this particular embodiment.

In this alternative embodiment, a plurality of slits can be formed in the flexible outer covering to provide a plurality of longitudinal strips. When the top end portion of the flexible covering is moved downwardly towards the bottom portion of the cylindrical container, the longitudinally extending strips will be thrust outwardly away from the side wall surface and apertures, and otherwise distorted or transformed into a structure enveloping a substantial portion of the cylindrical fragrance container. When the dispenser is opened, the resulting enveloping structure will comprise an arrangement of longitudinally distorted strips which are spaced substantially uniformly about the cylindrical container, and form passages between the adjacent longitudinal strips. In such a configuration, fragrance vapor within the container will be permitted to flow freely and passively through the apertures and passages of the enveloping structure to the ambient environment.

In other embodiments it is possible to support fragrance producing material from either one or both of the end caps of the fragrance dispenser. While the particular embodiments shown and described above have proven to be useful in many applications involving the fragrance dispensing art, further modification of the present invention will occur to persons skilled in the art. These modifications are necessarily within the scope and spirit of the present invention defined by the following claims.

What is claimed is:

1. A dispenser for releasing a fragrance to an ambient environment comprising:
   a container for storing a fragrance releasing substance which produces fragrance vapor, said container having a first end and second end and further having a side wall surface with one or more apertures formed therein; and
   a flexible covering disposed over said side wall surface and having a plurality of slits formed therein, said flexible covering occluding said apertures when said flexible covering is disposed over said side wall surface, said flexible covering being fixedly attached to a portion of said side wall surface and having a free portion which is slidable relative to said side wall surface so as to distort into a structure enveloping a substantial portion of said container and providing a plurality of passages, whereby fragrance vapor within said container is permitted to flow freely through said apertures in said container and through said passages of said enveloping structure to said ambient environment.

2. The dispenser of claim 1, wherein said passages of said enveloping structure have dimensions which can be varied in response to movement of said flexible covering relative to said side wall surface.

3. The dispenser of claim 2, wherein said enveloping structure comprises a plurality of flexible strips spaced substantially uniformly about said container and forming said passages between adjacent flexible strips, each said strip having a lower end portion connected to a portion of said flexible covering which is fixedly attached to said side wall surface, and an upper end portion of said flexible covering which is free to slide relative to said side wall surface.

4. The dispenser of claim 1, wherein said container has a cylindrical geometry, and said plurality of slits extends helically about said cylindrical container and divides said flexible covering into a plurality of helical strips.

5. The dispenser of claim 4, wherein said first end is proximate said fixed attachment of said flexible covering to said side wall surfaces, and wherein an annular recess is formed in said side wall surface at said second end, and an annular ring is rotatably disposed within said annular recess and fixedly attached to an adjacent portion of said flexible covering so that when said annular ring is rotated a selected amount within said annular recess, said plurality of helically extending strips are distorted into said enveloping structure, with said passages being formed between adjacent helical strips.

6. The dispenser of claim 5 wherein said annular ring has an inner bearing surface, and said annular recess has an outer bearing surface, each having respective surface textures which in contact with each other provides frictional engagement between said annular recess and said annular ring.

7. The dispenser of claim 6, wherein said first end of the container is closed off by a first end cap having an annular flange for retaining said annular ring within said annular recess.

8. The dispenser of claim 1, which further comprises a substance stored in said container which releases fragrance vapor when exposed to air.

9. The dispenser of claim 4, which further comprises a substance stored in said container which releases fragrance vapor when exposed to air.

10. The dispenser of claim 8, wherein said substance is wrapped in batting and inserted within said container.

11. The dispenser of claim 10, wherein said substance comprises one or more tablets impregnated with a fragrance oil.

* * * * *